(12) United States Patent
Berd

(10) Patent No.: US 7,297,330 B2
(45) Date of Patent: Nov. 20, 2007

(54) LOW DOSE HAPTENIZED TUMOR CELL AND TUMOR CELL EXTRACT IMMUNOTHERAPY

(75) Inventor: David Berd, Wyncote, PA (US)

(73) Assignee: Thomas Jefferson University, Philadelphia, PA (US)

( * ) Notice: Subject to any disclaimer, the term of this patent is extended or adjusted under 35 U.S.C. 154(b) by 832 days.

(21) Appl. No.: 09/776,250

(22) Filed: Feb. 1, 2001

(65) Prior Publication Data

US 2002/0009469 A1 Jan. 24, 2002

Related U.S. Application Data

(60) Provisional application No. 60/259,501, filed on Jan. 3, 2001, provisional application No. 60/180,258, filed on Feb. 4, 2000.

(51) Int. Cl.
- A01N 63/00 (2006.01)
- A61K 35/12 (2006.01)
- A61K 31/66 (2006.01)

(52) U.S. Cl. .................. 424/93.7; 424/573; 514/110
(58) Field of Classification Search ............. 424/93.7, 424/93.71; 435/325, 366
See application file for complete search history.

(56) References Cited

U.S. PATENT DOCUMENTS

| | | | |
|---|---|---|---|
| 5,290,551 A | 3/1994 | Berd | |
| 5,487,982 A | 1/1996 | Salter | |
| 5,747,269 A | 5/1998 | Rammensee et al. | |
| 5,827,516 A | 10/1998 | Urban et al. | |
| 6,458,369 B1 | 10/2002 | Berd | |

FOREIGN PATENT DOCUMENTS

| | | | |
|---|---|---|---|
| WO | WO 92/00101 | * | 1/1992 |
| WO | WO 96/40173 | | 12/1996 |
| WO | WO 98/14206 | | 4/1998 |
| WO | WO 98/34641 | * | 8/1998 |
| WO | WO 99/40925 | | 8/1999 |
| WO | WO 99/52546 | | 10/1999 |
| WO | WO 99/56773 | | 11/1999 |
| WO | WO 00/09140 | | 2/2000 |
| WO | WO 00/29554 | | 5/2000 |
| WO | WO 00/31542 | | 6/2000 |
| WO | WO 00/38710 | | 7/2000 |

OTHER PUBLICATIONS

Martin et al, PNAS, 1971, vol. 68, pp. 469-472.*
Berd et al, Ann NY Acad Sci, 1993, vol. 690, pp. 147-152.*
Fujiwara et al, The Journal of Immunology, 1980, vol. 124, pp. 863-869.*
Paul, Fundamental Immunology (text), 1993, pp. 1158-1159.*
Yu and Resifo, Journal of Clinical Investigation, 2002, vol. 110, pp. 289-294.*
Berd, Expert Review of Vaccines, 2004, vol. 3, pp. 521-527.*
Berd, Seminars in Oncology, Dec. 1998, vol. 25, pp. 605-610.*
Berd, Vaccine, 2001, vol. 19, pp. 2565-2570.*
Sato et al, Clinical Immunology and Immunopathology, 1995, vol. 74, pp. 35-43.*
Hanas and Leskowitz, Cellular Immunology, 1980, vol. 54, pp. 241-247.*
St. Bernard, Encyclopaedia Britanica 2006. Encyclopaedia Britaannica Online. Jan. 19, 2006 <http://www.search.eb.com/eb/article-9064811>.*
Berd et al. (Cancer Research, 1986, vol. 46, pp. 2572-2577).*
U.S. Appl. No. 09/304,859, filed May 4, 1999, Berd.
Bach et al., J. Immunol., 1978;121(4):1460-1468.
Berd et al., Cancer Res 1991;51:2731.
Berd et al., Cancer Res 1986;46:2572.
Miller and Claman, J. Immunol 1976;117(5):1519.
Nahas and Leskowitz, Cellular Immunol., 1980;54:241-247.
Rötzschke et al., Nature 1990;348:252.
Sato, Cancer Immunol Immunotherapy 1996;43:174.
Sherman et al., J. Immunol., 1978;121:1432.
Weigle, J. Exp. Med., 1965;122:1049-1063.
D. Berd et al., U.S. Appl. No. 08/203,004, filed Feb. 28, 1994.
D. Berd et al., U.S. Appl. No. 08/479,016, filed Jun. 7, 1995.
David Berd, U.S. Appl. No. 08/899,905, filed Jul. 24, 1997.
David Berd, U.S. Appl. No. 08/942,794, filed Oct. 2, 1997.
D. Berd et al., U.S. Appl. No. 09/447,897, filed Nov. 23, 1999.
Sato et al., Cancer Invest., 1997;15:98-105.
Kim et al., Eur. J. Immunol., 1992;22:775-782.
Sherman et al., J. Immunol., 1978;121:1432-1436.
Grabbe et al., Immunol.Today, 1995;16:117-121.
Siena et al., Exp. Hematol., 1995;23:1463-1471.
Sahasrabudhe et al., J. Immunol., 1993;151:6302-6310.
Shamamian et al., Cancer Immunol. Immunother., 1994;39:73-83.
Cox et al., Science, 1994:264:716-719.

(Continued)

Primary Examiner—Karen A. Canella
(74) Attorney, Agent, or Firm—Morgan, Lewis & Bockius LLP

(57) ABSTRACT

This invention relates to compositions comprising haptenized tumor cells and extracts thereof, methods for preparing the compositions, vaccines comprising such haptenized tumor cells, and methods for treating cancer with such vaccines. In a specific embodiment, melanoma cells are haptenized with a dinitrophenyl group, and used for treatment of melanoma patients having metastatic disease. Preferably, patients are given a first vaccine dose containing haptenized cells to "prime" the immune system. Subsequently, patients are injected with an immunomodulatory compound such as cyclophosphamide. In a preferred embodiment, an appropriate time period after the "priming" vaccine dose, additional vaccine doses containing a mixture of haptenized cells and an adjuvant are administered. The described treatment plan is more effective for eliciting favorable anti-tumor immune responses.

20 Claims, 2 Drawing Sheets

OTHER PUBLICATIONS

Peoples et al., J. Immunol., 1993;151:5481-5491.
Jerome et al., Cancer Res., 1991;51:2908-2916.
Morioka et al., J. Immunol., 1994;153:5650-5658.
Burrows et al., J. Neurosci. Res. 1997;49:107-116.
Gavin et al., Eur. J. Immunol., 1994;24:2124-2133.
Edman et al., Eur. J. Bio-chem., 1967;1:80-91.
Kempkes et al., J. Immunol., 1991;147:2467-2473.
Jang et al., Eur. J. Immunol., 1991;21:1303-1310.
Pistoor et al., J. Invest. Dermatol., 1995;105:92-95.
Nalefski and Rao, J. Immunol., 1993;150:3806-3816.
Carlsson, et al., Biochem J., 1978;173:723-737.
Miller et al., J. Immunol., 1976;117:191-196.
Brown, "Albumin structure, function and uses", Rosenoer, V.M. et al. (eds.), Pergamon Press:Oxford, pp. 27-51, 1977.
Weitkamp, L.R., et al., Ann. Hum. Genet., 1973;37:219-226.
Hood et al., "Tolerance and the Regulation of Immunity", Second Edition, 1984, Benjamin-Cummings: Menlo Park, CA, pp. 366-401.
McCune et al., Cancer, 1979;43:1619-1623.
Pulaski et al., Cancer Res., 1998;58:1486-1493.
Berd et al., J. Clin. Oncol., 1997;15:2359-2370.
Rennke et al., Kidney International, 1994;45:1044-1056.
Heppner et al., Cancer Res. 1978;38:3758-3763.
Miller et al., Cancer Res., 1981;41:3863-3867.
Miller, Invasion Metastasis, 1981;1:220-226.

* cited by examiner

FIG. 1A

| | -42f to -30 | -20‡ to -3 | -12 to -3 | 1 | 7 | 10 | 17 | 24 | 31 | 38 | 45 | | | | | | | | | | | | |
|---|---|---|---|---|---|---|---|---|---|---|---|---|---|---|---|---|---|---|---|---|---|---|---|
| Day of Study | | | | | | | | | | | | | | | | | | | | | | | |
| Week of Study | | | | | 1 | 2 | 3 | 4 | 5 | 6 | 7 | | | | | | | | | | | | |
| Month of Study | | | | | | | | | | | 1 | 2 | 3 | 4 | 5 | 6 | 7 | 8 | 9 | 10 | 11 | 12 | |
| Surgery | X | | | | | | | | | | | | | | | | | | | | | | |
| Informed Consent | | X | | | | | | | | | | | | | | | | | | | | | |
| Randomize | | | X | | | | | | | | | | | | | | | | | | | | |
| Cyclophosphamide | | | | | X | | | | | | | | | | | | | | | | | | |
| BCG | | | | | | XA | XA | XB | XB | XC | XC | | | | | | XC | | | | | | |
| Vaccine | | | | | | | | | | | X | | | | | X | | | | | | | |
| History/Physical Exam | | | | X | | X | X | X | X | X | X | Xe | Xe | Xe | Xe | Xe | Xe | Xe | Xe | Xe | Xe | Xe | * |
| Vital Signs | | | | X | | X | X | X | X | X | X | Xe | Xe | Xe | Xe | Xe | Xe | Xe | Xe | Xe | Xe | Xe | * |
| Performance Status | | | | X | | X | X | X | X | X | X | Xe | Xe | Xe | Xe | Xe | Xe | Xe | Xe | Xe | Xe | Xe | * |
| Routine Labs ‡‡ | | | | X | | X | X | X | X | X | X | Xe | Xe | Xe | Xe | Xe | Xe | Xe | Xe | Xe | Xe | Xe | * |
| Pregnancy (HCG) | | | | X | | | | | | | | | | | | | | | | | | | |
| Hepatitis/HIV | | | | X | | | | | | | | | | | | | | | | | | | |
| Chest X-Ray | | | | | | | | | | | | | Xe | | | Xe | | Xe | | Xe | | | * |
| CT or MRI | | | | X | | | | | | | | | | Xe | | | Xe | | | | | | Xe | * |

† This can be extended up to -56 days only if an additional procedure is needed to establish that the patient is melanoma-free prior to randomization \* History/Physical Exam, Vital Signs, Performance Status, Routine Labs, Chest X-Ray q2 months in year 2, q3 months in year 3, then q6 months through year 5; CT or MRI at 18, 24, and 36 months (chest x-ray omitted if CT/MRI scheduled)

XA 0.1mL of a 1:10 dilution of Tice BCG (Tice-A) mixed with vaccine

XB 0.1 mL of a 1:100 dilution of Tice BCG (Tice-B) mixed with vaccine

XC 0.1 mL of a 1:1000 dilution of Tice BCG (Tice-C) mixed with vaccine

‡ This can be extended up to -34 days if an additional procedure is needed to establish that the patient is melanoma-free prior to randomization ‡‡ Routine Labs: hematology (CBC with differential, platelet count), BUN or creatinine, LDH, SGOT, alkaline phosphatase, electrolytes <e End of Treatment Month

LOW DOSE HAPTENIZED TUMOR CELL AND TUMOR CELL EXTRACT IMMUNOTHERAPY

This patent application claims the priority of U.S. provisional patent application No. 60/180,258, filed on Feb. 4, 2000, and 60/259,501, filed on Jan. 3, 2001, which is incorporated herein by reference.

FIELD OF THE INVENTION

The invention relates to compositions comprising haptenized tumor cells and extracts thereof. The invention also relates to methods for treating cancer in which a priming dose of a hapten-modified tumor cell preparation is administered prior to any immunomodulatory agent that potentiates protective anti-tumor immunity or inhibits immune suppression, or both, such as, e.g., cyclophosphamide, and prior to compositions comprising a mixture between an immunological adjuvant and haptenized tumor cells or tumor cell extracts.

BACKGROUND OF THE INVENTION

Haptenized Tumor Cell Vaccines

An autologous whole-cell vaccine modified with the hapten dinitrophenyl (DNP) has been shown to produce inflammatory responses in metastatic sites of melanoma patients. The survival rates of patients receiving post-surgical adjuvant therapy with DNP-modified vaccine are markedly higher than those reported for patients treated with surgery alone. Intact cells are preferred for the vaccine.

U.S. Pat. No. 5,290,551, to David Berd, discloses and claims vaccine compositions comprising haptenized melanoma cells. Melanoma patients who were treated with these cells developed a strong immune response. This response was detected, e.g., in a delayed-type hypersensitivity (DTH) response to haptenized and non-haptenized tumor cells. More importantly, the immune response to non-haptenized cells has been associated with an increased survival rate of melanoma patients.

Haptenized tumor cell vaccines have also been described for other types of cancers, including lung cancer, breast cancer, colon cancer, pancreatic cancer, ovarian cancer, and leukemia (see U.S. patent application Ser. No. 08/203,004, filed Feb. 28, 1994; PCT Publication Nos. WO 96/40173 and WO 98/14206, and PCT Application No. PCT/US98/16660).

Generally, the immune response to haptenized cells has been found to be independent of the choice of hapten, but dependent on the functional group to which the hapten is attached. In particular, it has been reported that haptenization of $\epsilon$-amino groups of lysine and —COOH groups of aspartic acid and glutamic acid is effective for a robust immune response (Nahas and Leskowitz, Cellular Immunol., 1980;54:241).

It is known from animal studies that immunization of mice with syngeneic lymphocytes modified with arsanilic acid induces strong T cell responses against those modified cells, including DTH (Bach et al., J. Immunol., 1978;121: 1460) and cytotoxic T cells (Sherman et al., J. Immunol., 1978;121 :1432). Injection of arsanilic acid into the rat kidney induced a brisk autoimmune nephritis (Rennke et al., Kidney International, 1994;45:1044). Obviously, the administration of even minute amounts of arsanilic acid into human is unacceptable, but sulfanilic acid, a non-toxic compound in small amounts, should induce a similar immunological effect (Nahas and Leskowitz, supra, 1980). Both compounds can be coupled to tyrosine and histidine after being diazotized by treatment with sodium nitrite. Moreover, immunization of animals with sulfanilic acid-modified protein can induce autoimmunity (Weigle, J. Exp. Med., 1965;122:1049). A third potentially interesting hapten in this category is phosphorylcholine (PC), in light of the work of Kim et al. (Eur. J. Immunol., 1992;22:775). However, it has not been established that these haptens will be effective in humans; on the contrary, Nahas and Leskowitz, supra, suggest otherwise.

These discoveries have led to rapid advances in the treatment of cancer, particularly melanoma, by immunotherapy. Nevertheless, there remains a need in the art for even more effective therapies, since the response rates achieved with the haptenized tumor cell vaccine technologies mentioned above, while impressive, have not reached 100%. There is also a need in the art for more effective treatment regimens which require substantially fewer haptenized cells per dose, either to permit more dosages or to provide an effective therapy with a smaller number of cells. This is especially critical for the treatment of an early stage or recurrent cancer, when the number of cells obtainable from a resected tumor may be fewer than necessary for vaccine preparation as described above.

The present invention addresses these and other needs in the art in a surprisingly effective way.

The citation of any reference herein should not be construed as an admission that such reference is available as "Prior Art" to the instant application.

SUMMARY OF THE INVENTION

The present invention advantageously provides a composition comprising haptenized tumor cells or tumor cell extracts, which may be used as a priming dose in a cancer treatment regimen intended to induce an anti-tumor response in a cancer patient.

According to one aspect, the present invention relates to a composition comprising a hapten modified mammalian, preferably human, tumor cell or tumor cell extract.

In another aspect, the present invention is directed to a composition comprising from about $2 \times 10^5$ to about $2.5 \times 10^6$ hapten modified mammalian tumor cell or cell equivalents.

In a further aspect, the present invention is directed to a method of treating cancer comprising administering to a mammal, preferably a human, a composition comprising hapten modified human tumor cell or tumor cell extract wherein said mammal suffers from a malignant tumor of the same type as said tumor cell membrane.

In a further embodiment, the invention is directed to a method of treating cancer comprising initiating the treatment by administering a first dose comprising hapten modified or unmodified tumor cells or tumor cell equivalents prior to the administration of any immunomodulatory agent that potentiates protective anti-tumor immunity or inhibits immune suppression, or both.

In another embodiment, the invention is directed to a method of treating cancer comprising initiating the treatment by administering a first dose comprising hapten modified or unmodified tumor cells or tumor cell equivalents, free from any adjuvant, prior to the administration of any immunomodulatory agent that potentiates protective anti-tumor immunity or inhibits immune suppression, or both.

In yet another embodiment, the invention is directed to a method of treating cancer comprising initiating the treatment by administering a first dose, comprising hapten modified or unmodified tumor cells or tumor cell equivalents and an adjuvant, prior to the administration of any immunomodulatory agent that potentiates protective anti-tumor immunity or inhibits immune suppression, or both.

In still another embodiment, the invention is directed to a method of treating cancer comprising initiating the treatment by administering a first dose comprising hapten modified or unmodified tumor cells or tumor cell equivalents. After an appropriate time period, immunomodulatory agents that potentiate protective anti-tumor immunity or inhibit immune suppression, or both, followed by additional vaccine preparations, which may include immunological adjuvants, are administered according to a chosen time schedule.

Thus, one object of the invention is to provide more effective treatment regimens in the field of cancer vaccines by priming the immune system with a haptenized or non-haptenized tumor cell preparation.

This and other aspects of the invention are further elaborated in the Detailed Description of the Invention and Examples, infra.

DESCRIPTION OF THE DRAWING

FIGS. 1A and 1B. Schedule of events in a clinical treatment regimen outlined according to the invention.

DETAILED DESCRIPTION OF THE INVENTION

The invention provides for improved treatment protocols for cancer therapies based on the administration of tumor cell vaccines, particularly those involving repeated injections of haptenized tumor cell preparations. Priming the immune system by administering a first dose containing a relatively low amount of hapten modified tumor cells or tumor cell extracts or non-haptenized tumor cells or tumor cell abstracts, with or without adjuvant, before treating with cyclophosphamide and repeated doses of haptenized tumor cell preparations with or without adjuvant, may result in an augmented immune response to unmodified tumor cells. This latter priming phenomenon has broad applications to improve tumor vaccine outcomes in general, i.e., whether or not the tumor cells or cell extracts (including purified tumor-associated antigen) are haptenized.

The work described herein has provided strong support for the idea that immunizing patients with hapten-modified tumor cells can induce immunity to unmodified tumor cells. Animal and human data indicate that a first (priming) administration of a low dose of haptenized or non-haptenized tumor cells or tumor cell extracts increases the efficacy of hapten-modified cells or cell extract immunotherapy of cancer. The present invention provides a rationale for achieving improved results in humans. More particularly, the invention permits a more effective anti-tumor immune response, e.g., as measured by DTH, tumor regression, prolongation of survival, etc.

The present invention is based, in part, on data from a newly developed animal model (described in co-depending application Ser. No. 60/180,257, filed on Feb. 4, 2000). In this model, an improvement in the therapeutic outcome of DNP-modified, irradiated, autologous tumor cell vaccine, preceded by low-dose cyclophosphamide, was observed when the mice were pretreated with a single dose of DNP-modified, irradiated, autologous tumor cells (free of the adjuvant *Bacille Calmette-Guerin*) prior to the low-dose cyclophosphamide treatment, and then subjected to vaccination with DNP-modified, irradiated, autologous tumor cells admixed with adjuvant. These results illustrate the potentiating effect of the pretreatment regimen for the vaccination protocol.

The present invention is based, in part, on data derived from human studies. An improvement in the therapeutic outcome of DNP-modified, irradiated, autologous tumor cell vaccine, preceded by low-dose cyclophosphamide, was observed when humans were pretreated with a single dose of DNP-modified or non-modified, irradiated, autologous tumor cells (free of the adjuvant *Bacille Calmette-Guerin*) prior to the low-dose cyclophosphamide treatment, and then subjected to vaccination with DNP-modified, irradiated, autologous tumor cells admixed with adjuvant. These results illustrate the potentiating effect of the pretreatment regimen for the vaccination protocol The various aspects of the invention will be set forth in greater detail in the following sections. This organization into various sections is intended to facilitate understanding the invention, and is in no way intended to be limiting thereof.

Definitions

The following defined terms are used throughout the present specification, and should be helpful in understanding the scope and practice of the present invention.

A "hapten-modified tumor cell preparation" refers either to haptenized tumor cells or tumor cell extract as described in greater detail herein.

The term "corresponds" is used to describe the number of cells in a composition or used to prepare the amount of a tumor cell extract in a composition (i.e., cell equivalents in the composition).

In a specific embodiment, the term "about" or "approximately" means within 50%, preferably within 25%, and more preferably within 10% of a given value or range. Alternatively, the term about means within an acceptable standard error of the mean, when considered by one of ordinary skill in the art.

A "formulation" refers to an aqueous medium or solution for the preservation or administration, or both, of haptenized tumor cells or tumor cell extracts, which is preferably directly injectable into an organism. The aqueous medium will include salts or sugars, or both, at about an isotonic concentration.

The phrase "pharmaceutically acceptable" refers to molecular entities, at particular concentrations, and compositions that are physiologically tolerable and do not typically produce an allergic or similar untoward reaction, such as gastric upset, fever, dizziness and the like, when administered to a human or non-human animal. Preferably, as used herein, the term "pharmaceutically acceptable" means approved by a regulatory agency of the Federal or a state government or listed in the U.S. Pharmacopoeia or other generally recognized pharmacopoeia for use in humans or non-human animals.

As used herein, the term "isolated" means that the referenced material is removed from the natural environment in which it is normally found. In particular, isolated biological material if free of cellular components. An isolated peptide may be associated with other proteins or nucleic acids, or both, with which it associates in the cell, or with cellular membranes if it is membrane-associated. An isolated organelle, cell, or tissue is removed from the anatomical site in which it is found in an organism. An isolated material may be, but need not be, purified.

The term "purified" as used herein refers to material that has been isolated under conditions that reduce or eliminate unrelated materials, i.e., contaminants. For example, a purified protein is preferably free of other proteins or nucleic acids with which it is associated in a cell; a purified cell is free of unrelated cells and tissue matrix components.

A composition "free of any adjuvant" is a composition, e.g., a haptenized tumor cell preparation, not containing an adjuvant or co-administered with an adjuvant, nor administered less than 24 hours before or after an adjuvant. This is also referred to as "adjuvant free."

A "subject" is a human or a non-human animal who may receive haptenized tumor cells formulated in a composition of the invention. Preferably the subject is a human. However, the invention is also contemplated for veterinary medicine, particularly for treatment of domestic pets (dogs, cats), and livestock (horses, cows, pigs, etc.)

An "anti-tumor response" is at least one of the following: tumor necrosis, tumor regression, tumor inflammation, tumor infiltration by activated T lymphocytes, delayed-type hypersensitivity (DTH) response, and Clinical Response.

A "composition", "vaccine composition" or a "tumor cell vaccine" are used herein interchangeably to refer to an admixture of a hapten-modified tumor cell preparation in a formulation, optionally with an adjuvant. In the context of an adjuvant-free first dose (priming) embodiment of the invention, the composition or vaccine may be modified, a mixture of modified and non-modified, or non-modified: tumor cells, tumor cell membranes (especially the plasma, i.e., extracellular membrane), or proteins or peptides extracted from the tumor cell.

The terms "vaccinate", "immune therapy", and "immunotherapy" are used herein interchangeably to refer to administration of a composition comprising a hapten-modified tumor cell preparation to treat a cancer, e.g., after surgical resection of the tumor.

An "anti-tumor response" includes, but is not limited to, one or more of the following: tumor necrosis, tumor regression, tumor inflammation, tumor infiltration by activated lymphocytes, activation of tumor infiltrating lymphocytes, DTH response (against tumor cells), and a Clinical Response.

The term "treat" means to attempt to elicit an anti-tumor response against cells of the tumor, i.e., the cancer.

Haptenized Tumor Cell Preparation

The present invention is directed for use in the preparation of haptenized tumor cell vaccines for treating cancer, including metastatic and primary cancers. Cancers treatable with the present invention include solid tumors and non-solid tumors, including hematologic malignancies. Examples of solid tumors that can be treated according to the invention include sarcomas, carcinomas, and other tumors such as, but not limited to: fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oligodendroglioma, meningioma, melanoma, neuroblastoma, and retinoblastoma. Hematologic malignancies include leukemias, lymphomas, and multiple myelomas. The following are non-limiting preferred examples of the cancers treatable with the composition and methods of the present invention: melanoma, including stage-4 melanoma; ovarian, including advanced ovarian; leukemia, including but not limited to acute myelogenous leukemia; colon, including colon metastasized to liver; rectal, colorectal, breast, lung, kidney, and prostate cancers.

Tumor Cells

The compositions of the present invention are prepared from tumor cells, e.g., cells obtained from tumors surgically resected in the course of a cancer treatment regimen as described above. Tumor cells or cell extracts to be used in the present invention are preferably prepared as follows. Tumors are processed as described by Berd et al., Cancer Res., 1986;46:2572, Sato, et al., Cancer Invest., 1997;15:98, U.S. Pat. No. 5,290,551, and applications U.S. Ser. Nos. 08/203,004, 08/479,016, 08/899,905, 08/942,794, or corresponding PCT Publication WO96/40173, each of which is incorporated herein by reference in its entirety. Briefly, the cells are extracted by dissociation, such as by enzymatic dissociation with collagenase and DNase, by mechanical dissociation in a blender, by teasing with tweezers, using mortar and pestle, cutting into small pieces using a scalpel blade, and the like. With respect to non-solid tumors, blood or bone marrow samples may be collected and tumor cells isolated by density gradient centrifugation.

The tumor cells of the present invention may be intact, attenuated, or killed cells. Tumor cells incapable of growth and division after administration into the subject, such that they are substantially in a state of no growth, are preferred for use in the present invention. It is to be understood that "cells in a state of no growth" means intact cells that will not divide. Conventional methods of rendering cells incapable of division are known to skilled artisans and may be useful in the present invention. For example, cells may be irradiated prior to use. Tumor cells may be irradiated to receive a dose of about 2500 cGy to prevent the cells from multiplying after administration. Alternatively, haptenization, and particularly dual haptenization, can render the cells incapable of growth.

The tumor cells should preferably originate from the same type of cancer as that to be treated, and are even more preferably syngeneic (e.g., autologous or tissue-type matched). For purposes of the present invention, syngeneic refers to tumor cells that are closely enough related genetically that the immune system of the intended recipient will recognize the cells as "self", e.g., the cells express the same or almost the same complement of MHC molecules. Another term for this is "tissue-type matched." For example, genetic identity may be determined with respect to antigens or immunological reactions, and any other methods known in the art. A syngeneic tumor cell can be created by genetically engineering a tumor cell to express the required MHC molecules.

Preferably the cells originate from the type of cancer which is to be treated, and, more preferably, from the same patient who is to be treated. The tumor cells may be, but are not limited to, autologous cells dissociated from biopsy or surgical resection specimens, or from tissue culture of such cells. Nonetheless, allogeneic cells and stem cells are also within the scope of the present invention.

Tumor Cell Membranes

The isolated, modified tumor cell membranes of the present invention are prepared from mammalian, preferably human, tumor cells. In one embodiment of the invention, tumor cell membrane are isolated from a tumor of an animal, e.g., from a feline, canine, equine, bovine, or porcine family. Isolation and preparation of haptenized tumor cell membranes is described in U.S. patent application Ser. No. 08/479,016, filed Jun. 7, 1995 and U.S. application Ser. No. 90/025,012, filed Feb. 17, 1998.

The tumor cells from which membranes are isolated may be intact, attenuated, or killed cells. Tumor cells rendered incapable of growth and division prior to administration into the patient, such that the cells are substantially in a state of no growth, can be used in the present invention. Alternatively, tumor cell membranes may also be isolated from tumor cells capable of in vivo growth and division, since the membranes by themselves cannot multiply. Preferably, in such a case, the tumor cell membrane preparation is not contaminated with tumor cells capable of multiplying in vivo.

As with tumor cells, tumor cell membranes are preferably isolated from the tumor cells of the same type of cancer as that to be treated. For example, membranes to be used for treating ovarian cancer are isolated from ovarian cancer cells. Preferably, the tumor cells originate from the same subject who is to be treated. The tumor cells are preferably syngeneic (e.g. autologous), but may also be allogeneic to that subject. There may be genetic identity between a particular antigen on the tumor cell used as a membrane source and an antigen present on the patient's tumor cells. The tumor cells may be, but are not limited to, cells dissociated from biopsy specimens or from tissue culture. Membranes isolated from allogeneic cells and stem cells are also within the scope of the present invention.

Tumor cell membranes may include all cellular membranes, such as outer membrane, nuclear membranes, mitochondrial membranes, vacuole membranes, endoplasmic reticular membranes, golgi complex membranes, and lysosome membranes. In one embodiment of the invention, more than about 50% of the membranes are tumor cell outer membranes. Preferably, more than about 60% of the membranes consist of tumor cell outer membranes, with more than about 70% being more preferred, 80% being even more preferred, 90% being even more preferred, 95% being even more preferred, and 99% being most preferred.

Preferably, the isolated membranes are substantially free of nuclei and intact cells. For example, a membrane preparation is substantially free of nuclei or intact cells if it contains less than about 100 cells and/or nuclei in about $2\times10^8$ cell equivalents (c.e.) of membrane material. A cell equivalent is that amount of membrane isolated from the indicated number of cells. An isolated tumor cell membrane which is substantially free of cells and/or nuclei may contain lymphocytes and/or lymphocyte membranes.

Preferably, the isolated tumor cell membranes are the outer cell membranes, i.e., tumor cell plasma membranes. The membrane preparation of the invention may contain the entire outer membrane or a fraction thereof. An isolated membrane of the invention, preferably including a fraction of the outer membrane, contains an MHC molecule fraction and/or a heat shock protein fraction. The size of the membrane fragments is not critical.

Allogeneic tumor cell membranes may also be used in the methods of the present invention with syngeneic (e.g. autologous) antigen presenting cells. This approach permits immunization of a patient with tumor cell membranes originating from a source other than the patient's own tumor. Syngeneic antigen-presenting cells process allogeneic membranes such that the patient's cell-mediated immune system may respond to them.

A tumor cell membrane (modified or un-modified) as referred to in this specification includes any form in which such a membrane preparation may be stored or administered, such as, for example, a membrane resuspended in a diluent, a membrane pellet, or a frozen or a lyophilized membrane.

The tumor cell membranes can be obtained from haptenized cells, or may be haptenized after extraction from the cells using the techniques described infra.

Tumor cell membranes are prepared from tumor cells, e.g., obtained as described above, by disrupting the cells using, for example, hypotonic shock, mechanical dissociation and enzymatic dissociation, and separating various cell components by centrifugation. Briefly, the following steps may be used: lysing tumor cells, removing nuclei from the lysed tumor cells to obtain nuclei-free tumor cells, obtaining substantially pure membranes free from cells and nuclei, and coupling the tumor cell membranes to a hapten to obtain hapten-modified tumor cell membranes. Membrane isolation may be conducted in accordance with the methods of Heike et al.

In one embodiment of the invention, intact cells and nuclei may be removed by consecutive centrifugation until membranes are substantially free of nuclei and cells, as determined microscopically. For example, lysed cells may be centrifuged at low speed, such as for example, at about 500-2,000 g for about five minutes. The separation procedure is such that less than about 100 cells or nuclei remain in about $2\times10^8$ cell equivalents (c.e.) of membrane material. The retrieved supernatant contains membranes which, for example, may be pelleted by ultracentrifugation at about 100,000 g for about 90 minutes. The pellet contains mainly membranes. Membranes may be resuspended, for example, in about 8% sucrose, 5 mM Tris, pH 7.6 and frozen at about −80° C. until use. Any diluent may be used, preferably one that acts as a stabilizer. To determine the quality of membrane preparation, a fraction (about $6\times10^7$ c.e. membranes) may be cultured regularly. Cell colonies should not develop and cells or nuclei should not be detected by light microscopy.

Modification of the prepared cells or membranes with DNP or another hapten may be performed by known methods, e.g. by the method of Miller and Claman (J. Immunol., 1976;117:1519) which involves a 30 minute incubation of tumor cells or membranes with a hapten under sterile conditions, followed by washing with sterile saline. Haptenmodification may be confirmed by flow cytometry using a monoclonal anti-hapten antibody.

The dissociated cells or isolated membranes may be used fresh or stored frozen, such as in a controlled rate freezer or in liquid nitrogen until needed. The cells and membranes are ready for use upon thawing. Preferably, the cells or membranes are thawed shortly before they are to be administered to a patient. For example, the cells or membranes may be thawed on the day that a patient is to be skin tested or treated.

Allogeneic tumor cell membranes may be prepared as described above. However, prior to administration to a subject the preparation may be co-incubated with syngeneic (e.g. autologous) antigen presenting cells. Syngeneic antigen-presenting cells process allogeneic membranes such that the patient's cell-mediated immune system may respond to them. This approach permits immunization of a patient with tumor cell membranes originating from a source other than the patient's own tumor. Allogeneic tumor cell membranes are incubated with antigen-presenting cells for a time period varying from about a couple of hours to about several days. The membrane-pulsed antigen presenting cells are then washed and injected into the patient.

Antigen-presenting cells may be prepared in a number of ways including for example the methods of Grabbe et al. (Immunol. Today, 1995;16:117-121) and Siena et al. (Exp. Hematol., 1995;23:1463-1471). Briefly, blood is obtained, for example by venipuncture, from the patient to be immunized. Alternatively, a sample of bone marrow may be collected. Alternatively, blood leukocytes may be obtained by leukapheresis. From any of these sources, mononuclear leukocytes are isolated by gradient centrifugation. The leukocytes may be further purified by positive selection with a monoclonal antibody to the antigen, CD34. The purified leukocytes are cultured and expanded in tissue culture medium (for example, RPMI-1640 supplemented with serum, such as fetal calf serum, pooled human serum, or autologous serum). Alternatively, serum-free medium may be used. To stimulate the growth of antigen-presenting cells, cytokines may be added to the culture medium. Cytokines include but are not limited to granulocyte macrophage-colony stimulating factor (GM-CSF), interleukin 4 (IL4), TNF (tumor necrosis factor), interleukin 3 (IL3), FLT3 ligand and granulocyte colony stimulating factor (G-CSF).

The antigen-presenting cells isolated and expanded in culture, for example, may be characterized as dendritic cells, monocytes, macrophages, and Langerhans cells.

Tumor Cell Peptides

The isolation of peptides to be used in hapten-modified anti-cancer vaccines is described in U.S. patent application Ser. No. 08/479,016, filed Jun. 7, 1995 and patent application Ser. No. 09/447,897, filed Nov. 24, 1998. Both applications disclose extraction and isolation of hapten-modified peptides, which can be adapted for the present invention. Peptides can also be synthesized based on known sequences, or isolated prior to haptenization. The isolated peptides can then be modified by dual-haptenization.

For purposes of the present invention, peptides are compounds of two or more amino acids and include proteins. Peptides will preferably be of low molecular weight, of about 1,000 kD to about 10,000 kD, more preferably about 1,000 kD to about 5,000 kD, which are isolated from a haptenized tumor cell and which stimulate T cell lymphocytes to produce gamma interferon. The peptide of the invention may be from about 8 to about 20 amino acids, preferably from about 8 to about 12 amino acids. In addition, the peptide is preferably haptenized. Peptides may be isolated from the cell surface, cell interior, or any combination of the two locations. The extract may be particular to type of cancer cell (versus normal cell). The peptides of the present invention include but are not limited to peptides which bind to MHC molecules, a cell surface-associated protein, a peptide associated with a heat shock protein/chaperonin, a protein encoded by cancer oncogenes, or mutated anti-oncogenes. In one preferred embodiment of the invention, peptides are bound to the MHC molecules. For purposes of the present invention "a peptide equivalent" is the peptide having the same amino acid sequence as the peptide isolated from an MHC molecule, although prepared either by degradation of a protein comprising the peptide, synthesized in vitro or recombinant DNA technology.

Preferably, the peptides are derived from tumor specific antigens. There is substantial evidence that the same T-cell-defined tumor antigens are expressed by different human melanoma tumors, suggesting that transformation-associated events may give rise to recurrent expression of the same tumor antigen in tumors of related tissue and/or cellular origin (Sahasrabudhe et al., J. Immunol., 1993;151:6302-6310; Shamamian et al., Cancer Immunol. Immunother., 1994;39:73-83; Cox et al., Science, 1994;264:716; Peoples et al., J. Immunol., 1993;151:5481-5491; Jerome et al., Cancer Res., 1991;51:2908-2916; Morioke et al., J. Immunol., 1994;153:5650-5658). Examples of such antigens include, but are not limited to, MART 1/Melan A, gp-100, and tyrosinase (melanoma); MAGE-1 and MAGE-3 (bladder, head and neck, non-small cell carcinoma); HPV E6 and E7 proteins (cervical cancer); HER2/neu/cerbB-2 (breast cancer); HER3, HER4, Mucin (MUC-1) (breast, pancreas, colon, prostate); prostate specific antigen (PSA) (prostate); and CEA (colon, breast, GI).

The cell extracts of the invention, including peptides originally isolated from MHC molecules located on tumor cell plasma membranes, have the property of stimulating T cells. For purposes of the present invention, stimulation refers to proliferation of T cells as well as production of cytokines by T cells in response to the cell extract. Proliferation of T cells may be observed by uptake by T cells of modified nucleic acids, such as but not limited to $^{3}$H thymidine, $^{125}$IUDR (iododeoxyuridine); and dyes such as 3-(4,5-dimethylthiazol-2-yl)-2,5-diphenyltetrazolium bromide (MTT) which stains intact cells. In addition, production of cytokines such as but not limited to γ-interferon (INFγ), tumor necrosis factor (TNF), and interleukin-2 (IL-2) may be tested. Production of cytokines is preferably in an amount greater than 15 picograms/ml, more preferably about 20 to about 30 picograms/ml, even more preferably about 50 picograms/ml. Alternatively, cytotoxicity assays can be used to evaluate T cell stimulation.

From the hapten-modified cells, peptides may be extracted, some of which are hapten-modified as a result of modifying the cells. Alternatively, extracted or synthetic peptides can be reacted with a hapten after isolation or synthesis. Protein extraction techniques known to those of skill in the art may be followed by antigen assays to isolate proteins or peptides effective for patient treatment. The methods of isolating cell extracts are readily known to those skilled in the art. Briefly, cancer cells are isolated from a tumor and cultured in vitro. A hapten preparation is added to the cultured cells in accordance with the method set forth above. Peptides are isolated from cells according to an established technique, e.g., the technique of Rötzschke et al., Nature. 1990;348:252, the disclosure of which is hereby incorporated by reference in its entirety. The cells are treated with a weak acid such as but not limited to trifluoroacetic acid (TFA). The cells are thereafter centrifuged and the supernatant is saved. Compounds having a molecular weight greater than 5,000 are removed from the supernatant by gel filtration (G25 Sepharose, Pharmacia). The remainder of the supernatant is separated on a reversed-phase HPLC column (Superpac Pep S, Pharmacia LKB) in 0.1% TFA using a gradient of increasing acetonitrile concentration; flow rate =1 ml/min, fraction size =1 ml. Fractions containing small peptides are collected by HPLC according to the method of Sambrook et al., Molecular Cloning: A Laboratory Manual, 2nd ed., Cold Spring Harbor Laboratory Press, Cold Spring Harbor, N.Y. (1989), concentrated, and frozen.

The HPLC fractions containing small peptides are screened for immunological activity, e.g., by allowing them to bind to autologous B lymphoblastoid cells which are then tested for their ability to stimulate tumor-specific T lymphocytes. T cells used for this testing are isolated from a human patient and propagated in vitro as described in PCT Publication No. WO98/14206. The peptides that stimulate T cells are then analyzed for their structure. For example, the peptides are sequenced using methods known in the art to determine their amino acid sequence. In one embodiment of the invention, the peptides are sequenced as a pool as described by Burrows et al (J. NeuroSci. Res., 1997;49:107-116) and Gavin et al. (Eur. J. Immunol., 1994;24:2124-33) to determine prevailing motifs. In another embodiment of the invention, the peptides are further separated using methods known in the art, such as HPLC, as described in U.S. Pat. Nos. 5,747,269; 5,487,982; 5,827,516 and 5,820,862 and sequenced. Sequencing is performed by using Edman degradation as described in Edman and Berg, Eur. J. Biochem., 1967;80:116-132, or any modification thereof known in the art. One powerful technique for characterizing isolated peptides is mass spectrometry.

Once the sequence of the peptides isolated from the MHC molecules is known, synthetic peptides having the same sequence are synthesized and used as a vaccine alone, presented on an antigen presenting cell and/or in combination with other extracts or whole cells using the methods described above. The equivalent peptides may also be produced recombinantly or by chemical degradation of proteins containing the isolated peptides.

In another embodiment, the structure of known peptides is altered by changing at least one amino acid and the so altered peptides are tested for their ability to stimulate T cells.

Haptenization

The tumor cells, membranes, or peptides can be haptenized. For purposes of the present invention, virtually any small molecule, including peptides, that can induce an immune response when conjugated to a carrier, may function as a hapten. A variety of haptens of different chemical structure have been shown to induce similar types of immune responses: e.g., dinitrophenyl (DNP); trinitrophenyl (TNP) (Kempkes et al., J. Immunol., 1991;147:2467); phosphorylcholine (Jang et al., Eur. J. Immunol., 1991;21:1303); nickel (Pistoor et al., J. Invest. Dermatol., 1995;105:92); and arsenate (Nalefski and Rao, J. Immunol., 1993;150:3806). Conjugation of a hapten to a cell may preferably be accomplished by conjugation via ε-amino groups of lysine or —COOH groups. This group of haptens include a number of chemically diverse compounds: halonitrobenzenes (including dinitrofluorobenzene, difluorodinitrobenzene, trinitrofluorobenzene), N-iodoacetyl-N'-(5-sulfonic-1-naphthyl) ethylene diamine, nitrobenzene sulfonic acids (including trinitrobenzenesulfonic acid and dinitrobenzene sulfonic acid), fluorescein isothiocyanate, arsenic acid benzene isothiocyanate, and dinitrobenzene-S-mustard (Nahas and Leskowitz, Cellular Immunol., 1980;54:241). Once familiar with the present disclosure, skilled artisans would be able to choose haptens for use in the present invention.

Haptens generally include a reactive group for conjugation to a substituent on an amino acid side chain of a protein or polypeptide (e.g., a free carboxylic acid group as in the case of aspartic acid or glutamic acid; the ε-amino group of lysine; the thiol moiety of cysteine; the hydroxyl group of serine or tyrosine; the imidazole moiety of histidine; or the aryl groups of tryptophan, tyrosine, or phenylalanine). As used herein, the term "reactive group" refers to a functional group on the hapten that reacts with a functional group on a peptide or protein. The term "functional group" retains its standard meaning in organic chemistry. These reactive groups on a hapten are termed herein the "hapten reactive group". Numerous hapten reactive groups are known, which interact with the substituents present on the side chains of amino acids that comprise peptides and proteins. Preferred examples of such reactive groups for conjugation to specific polypeptide substituents are carboxylic acid or sulfonic acid derivatives (including acid chlorides, anhydrides, and reactive carboxylic esters such as N-hydroxysuccinimide esters), imidoesters, diazonium salts, isocyanates, isothiocyanates halonitrobenzenes, α-halocarbonyl compounds, maleimides, sulfur mustards, nitrogen mustards, and aziridines.

Functional Groups Reactive with Primary Amines. Hapten reactive groups that would form a covalent bond with primary amines present on amino acid side chains would include, but not be limited to, acid chlorides, anhydrides, reactive esters, α,β-unsaturated ketones, imidoesters, and halonitrobenzenes. Various reactive esters with the capability of reacting with nucleophilic groups such as primary amines are available commercially, e.g., from Pierce (Rockford, Ill.).

Functional Groups Reactive with Carboxylic Acids. Carboxylic acids in the presence of carbodiimides, such as EDC, can be activated, allowing for interaction with various nucleophiles, including primary and secondary amines. Alkylation of carboxylic acids to form stable esters can be achieved by interaction with sulfur or nitrogen mustards, or haptens containing either an alkyl or aryl aziridine moiety.

Functional Groups Reactive with Aromatic Groups. Interaction of the aromatic moieties associated with certain amino acids can be accomplished by photoactivation of aryl diazonium compound in the presence of the protein or peptide. Thus, modification of the aryl side chains of histidine, tryptophan, tyrosine, and phenylalanine, particularly histidine and tryptophan, can be achieved by the use of such a reactive functionality.

Functional Groups Reactive with Sulfhydryl Groups. There are several reactive groups that can be coupled to sulfhydryl groups present on the side chains of amino acids. Haptens containing an α,β-unsaturated ketone or ester moiety, such as maleimide, provide a reactive functionality that can interact with sulfhydryl as well as amino groups. In addition, a reactive disulfide group, such as 2-pyridyldithio group or a 5,5'-dithio-bis-(2-nitrobenzoic acid) group is also applicable. Some examples of reagents containing reactive disulfide bonds include N-succinimidyl 3-(2-pyridyl-dithio) propionate (Carlsson, et al., Biochem J., 1978;173:723-737), sodium S-4-succinimidyloxycarbonyl-alpha-methylbenzylthiosulfate, and 4-succinimidyloxycarbonyl-alpha-methyl-(2-pyridyldithio)toluene. Some examples of reagents comprising reactive groups having a double bond that reacts with a thiol group include succinimidyl 4-(N-maleimidomethyl)cyclohexahe-1-carboxylate and succinimidyl m-maleimidobenzoate.

Other functional molecules include succinimidyl 3-(maleimido)propionate, sulfosuccinimidyl 4-(p-maleimido-phenyl)butyrate, sulfosuccinimidyl 4-(N-maleimidomethyl-cyclohexane)-1-carboxylate, maleimidobenzoyl-N-hydroxysuccinimide ester. Many of the above-mentioned reagents and their sulfonate salts are available from Pierce.

Haptens also include a hapten recognition group that interacts with antibody. The recognition group is irreversibly associated with the hapten reactive group. Thus, when the hapten reactive group is conjugated to a functional group on the target molecule, the hapten recognition group is available for binding with antibody. By selecting an appropriate hapten reactive group, antibody recognition of, and binding to, a hapten recognition group can be made independent of the functional group to which the hapten is conjugated. When this is the case, the haptens are functionally equivalent, and are said to share antibody binding features. Naturally, in cases where the recognition groups of two haptens differ chemically, the reactive groups may be the same or different, i.e., reactive with the same or different functional groups on the target molecule.

Examples of different hapten recognition groups include without limitation to trinitrophenyl, fluorescein, other aromatics, phosphorylcholine, peptides, advanced glycosylation endproducts (AGE), carbohydrates, etc.

In a specific embodiment, the same hapten recognition group can be coupled to different amino acids through different hapten reactive groups. For example, the reagents dinitrobenzene sulfonic acid, dinitro-phenyldiazonium, and dinitrobenzene-S-mustard, all form the dinitrophenyl hapten coupled to amino groups, aromatic groups, and carboxylic acid groups, respectively. Similarly, an arsonic acid hapten can be coupled by reacting arsonic acid benzene isothiocyanate to amino groups or azobenzenearsonate to aromatic groups. In another specific embodiment, tumor cells or cell extracts are conjugated with two haptens by derivitization of two different functional groups. For example, a tumor cell preparation may be dual-haptenized with a DNP group coupled to ε-amino groups, and with a sulfanilic acid group coupled to aromatic side chains of histidine and tyrosine.

Isolation and Haptenization of Tumor Cells

The dissociated cells, cell membranes, or peptides may be stored frozen in a freezing medium (e.g., prepared from a sterile-filtered solution of 50 ml Human Serum Albumin (HSA) (American Red Cross) added to 450 ml of RPMI 1640 (Mediatech) supplemented with L-glutamine and adjusted to an appropriate pH with NaOH), such as in a controlled rate freezer or in liquid nitrogen until needed. The cells are ready for use upon thawing. Preferably, the cells are thawed shortly before haptenization. Optionally, the cells may be washed, and optionally irradiated to receive a dose of about 2500 cGy. They may then be washed again and suspended in Hanks Balanced Salt Solution (HBSS) without phenol red and without HSA.

Modification of the prepared cells with DNP or another hapten may be performed by known methods, e.g. by the method of Miller and Clanian (J. Immunol., 1976;117:151), incorporated herein by reference in its entirety, which involves a 30 minute incubation of tumor cells with DNFB under sterile conditions, followed by washing with sterile saline or HBSS/HSA.

Vaccine Preparations

The compositions of the invention may be administered in a mixture or in combination with a pharmaceutically-acceptable carrier, selected with regard to the intended route of administration and standard pharmaceutical practice. Dosages may be set with regards to weight, and the clinical condition of the patient. The proportional ratio of active ingredient to carrier naturally depend on the chemical nature, solubility, and stability of the compositions, as well as the dosage contemplated. The amount of the tumor cells of the invention to be used depend on such factors as the affinity of the compound for cancer cells, the amount of cancer cells present, and the solubility of the composition. The compounds of the present invention may be administered by any suitable route, including inoculation and injection via, for example, intradermal, intravenous, intraperitoneal, intramuscular, and subcutaneous routes.

In a preferred embodiment of the invention, the composition to be used for the first "priming" dose comprises a vaccine comprising about $2\times10^5$ to $2.5\times10^6$, more preferably less than about $2\times10^6$, even more preferably less than about $1\times10^6$, growth-incapacitated tumor cells or tumor cell equivalents suspended in a pharmaceutically acceptable carrier or diluent, such as but not limited to Hanks solution, saline, phosphate-buffered saline (PBS), and water, and optionally with adjuvant. The composition may be administered by intradermal injection into from one to about three contiguous sites per administration on the upper arms or legs, excluding limbs ipsilateral to a lymph node dissection. Vaccine preparations for subsequent administrations can comprise from about $2\times10^5$ to about $1\times10^7$ tumor cells or tumor cell equivalents, preferably from about $1\times10^6$ to about $2.5\times10^6$ tumor cells or tumor cell equivalents.

Formulations

The formulations according to the invention may be prepared in various ways. The different components may be mixed together, and then added to haptenized tumor cells or tumor cell equivalents. It is also possible to mix one or several of the components with the haptenized tumor cell preparation and then add the remaining component(s). The preparation of the formulation and its addition of the haptenized tumor cells are preferably performed under sterile conditions.

The respective proportions of the components of the media according to the invention may be adapted by persons skilled in the art.

Generally, for human tumor cells, HSA will be added to an appropriate buffered cell culture medium. "Human serum albumin" or "HSA" refers to a non-glycosylated monomeric protein consisting of 585 amino acid residues, having a molecular weight of about 66 kD. Its globular structure is maintained by 17 disulfide bridges, which create a sequential series of 9 double loops (Brown, "Albumin structure, function and uses", Rosenoer, V. M. et al. (eds.), Pergamon Press:Oxford, pp. 27-51, 1977). The genes encoding for HSA are known to be highly polymorphic, and more than 30 apparently different genetic variants have been identified by electrophoretic analysis (Weitkamp, L. R. et al., Ann. Hum. Genet., 1973;37:219-226). The HSA gene comprises 15 exons and 14 introns corresponding to 16,961 nucleotides from the putative mRNA "capping" site up to the first site of addition of poly(A). Autologous serum albumins can be used in the preparation of tumor cells from other animal species.

In its essence, a buffered cell culture medium is an isotonic buffered aqueous solution, such as phosphate buffered saline, Tris-buffered saline, or HEPES buffered saline. In a preferred embodiment, the medium is plain Hank's medium (no phenol red), e g., as sold commercially by Sigma Chemical Co. (St. Louis, Mo., USA). Other tissue culture media can also be used, including basal medium Eagle (with either Earle's or Hank's salts), Dulbecco's modified, Eagle's medium (DMEM), Iscove's modified Dulbecco's medium (IMDM), Medium 199, Minimal Essential Medium (MEM) Eagle (with Earle's or Hank's salts), RPMI, Dulbecco's phosphate buffered salts, Earle's balanced salts (EBSS), and Hank's Balanced Salts (HBSS). These media can be supplemented, e.g., with glucose, Ham's nutrients, or HEPES. Other components, such as sodium bicarbonate and L-glutamine, can be specifically included or omitted. Media, salts, and other reagents can be purchased from numerous sources, including Sigma, Gibco, BRL, Mediatech, and other companies. For use in humans, an appropriate medium is pharmaceutically acceptable.

Preferably, a formulation of whole, intact cells comprises an optimized HSA concentration in a buffered cultured medium, preferably HBSS. In a specific embodiment, the final concentration of HSA is about 1.0% in a HBSS. However, an unexpected improvement in cell viability can be achieved using at least about 0.25% HSA, a greater improvement in cell viability with 0.3% HSA (as compared to 0.1% HSA), and an even greater improvement is possible using at least about 0.5% HSA. Upper limits to the concentration are determined by the need to avoid contaminants that may be present in naturally-derived HSA, or alternatively to avoid allergic reactions to recombinant HSA. Preferably, the concentration of HSA in a formulation of the invention is no more than about 10%. More preferably, the concentration is less than or equal to about 5% and, more preferably still, less than or equal to about 2%.

Also, a composition or formulation of the invention may contain other components in addition to HSA to further stabilize the haptenized tumor cells. Examples of such components include, but are not limited to, carbohydrates and sugars, such as dextrose, sucrose, glucose, and the like, e.g., at a 5% concentration; medium to long chain polyols, such as glycerol, polyethylene glycol, and the like, e.g., at 10% concentration; other proteins; amino acids; nucleic acids; chelators; proteolysis inhibitors; preservatives; and other components. Preferably, any such constituent of a composition of the invention is pharmaceutically acceptable.

Adjuvant

In preferred embodiment, the tumor cell vaccines administered, including the "priming" dose, may be administered with an immunological adjuvant. The term "adjuvant" refers to a compound or mixture that enhances the immune response to an antigen (Hood et al., Immunology, Second Edition, 1984, Benjamin-Cummings: Menlo Park, Calif., p. 384). While commercially available pharmaceutically acceptable adjuvants are limited, representative examples of adjuvants include *Bacille Calmette-Guerin* (BCG) the synthetic adjuvant QS-21 comprising a homogeneous saponin purified from the bark of *Quillaja saponaria* and *Corynebacterium parvum* (McCune et al., Cancer, 1979;43: 1619). Other adjuvants include Complete and Incomplete Freund's Adjuvant, detoxified endotoxins, mineral oils, surface active substances such as lipolecithin, pluronic polyols, polyanions, peptides, and oil or hydrocarbon emulsions. In some cases, immunostimulatory compounds, as exemplified below, may function asadjuvants.

It will be understood that the adjuvant is subject to optimization. In other words, the skilled artisan can engage in experimentation that is no more than routine to determine the best adjuvant to use.

Immunomodulators and Combination Therapies

Treatment regimens for haptenized tumor cells or tumor cell extracts may include immunodulators, i.e. drugs that alter, suppress or strengthen the body's immune system. The immunomodulators can be generally subdivided into groups according to function, as listed below. However, it is to be understood that exemplified immunomodulatory compounds may serve different functions depending on cell-type, dosage, formulation, administration route, treatment regimen, and the patients condition. Immunopotentiators herein refers to compounds that potentiate the immune system for treatment with a tumor vaccine. Preferably, immunopotentiators at least temporarily diminish any down-regulation of anti-tumor responses evoked by haptenized tumor cells or cell extracts according to the present invention, the down-regulation involving, e.g., T suppressor cells; while to a lesser extent affecting other parts of the immune system. A preferred example of such a compound included is cyclophosphamide. Cyclophosphamide is preferably administered at doses lower than about 1000 mg/m$^2$, or, more preferably, at doses of about 300 mg/m$^2$. Immunosuppressants include, but is not limited to, chemotherapeutic agents known in the art, preferably administered at doses inducing a general suppression of the immune system. Immunostimulants is a general term encompassing endotoxin and endogenous agents, e.g., cytokines and lymphokines, including but not limited to IL-2, IL-4, INFγ, IL-12, and GM-CSF. According to the present invention, immunomodulators may be administered alone, mixed, or co-administered with the haptenized tumor cell vaccine, as appropriate. The tumor cells and extracts of the invention may also be used in conjunction with other cancer treatments including, but not limited to, chemotherapy, radiation therapy, immunotherapy, and gene therapy.

Clinical Response Criteria

Standard criteria for evaluating treatment response include: Complete response, which indicates complete disappearance of all metastases for at least about one month, more preferably for at least about three months, without development of new metastases; Partial response, which indicates at least about 50% reduction in the mean diameter of a measurable metastasis for at least about one month, more preferably for at least about three months, without development of new metastases; and Mixed response, which indicates at least about 50% reduction in the mean diameter of a measurable metastasis with concomitant growth of another metastasis. Stable disease indicates more than about 25% increase in the mean diameter of any measurable metastasis. Prolongation of time to relapse or of survival are both also examples of possible clinical response criteria.

EXAMPLES

The following examples are illustrative of the invention, but not limiting thereof.

Example 1

Treatment Protocol for Melanoma Patients

Patient group. The treatment efficacy of DNP-modified autologous melanoma cells (vaccine) is studied in post-surgical stage III melanoma patients having metastatic lymph node involvement, or stage IV melanoma patients with lung metastases. Prior to the initiation of the vaccine treatment, preferably within two months from the starting point, one or more tumor masses are surgically resected from each patient. For axillary nodes, a formal axillary node dissection is performed. For inguinal nodes, a superficial inguinal dissection is performed, with a deep dissection at the discretion of the surgeon. For other lymph node-bearing areas, an appropriate node dissection is performed. An adequate tumor sample, approximately 2 cm or 5 g, yielding at least about $50 \times 10^6$ cells, is kept under sterile conditions to be used for vaccine preparation. Patients are preferably confirmed melanoma-free by computed tomography (CT) or magnetic resonance imaging (MRI).

Vaccine preparation. The vaccine is prepared from a cryopreserved cell suspension, previously prepared from a portion of the patient's excised lymph node tumor mass, for delivery on the same day as the treatment. Cells are prepared and haptenized as described previously (see "Detailed Description" in the instant application; Berd et al., Cancer Res 1986;46:2572-7; U.S. Pat. No. 5,290,551; U.S. patent applications Ser. No. 08/203,004; Ser. No. 08/475,016; and Ser. No. 08/899,905). After haptenization and washing, the cells are suspended in HBSS supplemented with 1% HSA and stored at 4° C.

Vaccine dose 1 consists of $(0.75\pm0.25)\times10^6$ DNP-modified, intact tumor cells suspended in 0.2-0.3 ml Hank's solution.

Vaccine doses 2-8 consists of $(2.5\pm0.75)\times10^6$ DNP-modified, intact tumor cells suspended in 0.2-0.3 ml Hanks solution. Vaccines for doses 2-8 are gently mixed with Tice Bacillus Calmette-Guérin (Tice BCG; substrain of the Pasteur Institute strain; Organon Teknika Corp.). BCG in the form of a lyophilized powder, is reconstituted with 1.0 ml of saline for injection without preservative to make the "stock Tice BCG" solution. The stock solution is used the same day as prepared. The second and third doses of vaccine will be mixed with 0.1 ml of a 1:10 dilution (in saline for injection without preservative) of the "stock Tice BCG" solution (Tice-A). The fourth and fifth vaccines will be mixed with 0.1 ml of a 1:100 dilution of the "stock Tice BCG" solution (Tice-B). The sixth and seventh vaccines, as well as the vaccine booster at 6 months, will be mixed with 0.1 ml of a 1:1000 dilution of the "stock Tice BCG" solution (Tice-C). The expected BCG reaction is an inflammatory papule with no more than small (<5 mm) central ulceration. If reactions are larger than this (greater than Grade 2; see Section 11.1), the dose of BCG for the next doses will be further reduced by one 10-fold increment (Tice-D). No more than two consecutive doses of Tice-A or Tice-B should be given.

Treatment outline. On Day 1, the first vaccine dose, containing haptenized cells free from adjuvant, is administered as a single intradermal injection into the same limb as for all subsequent vaccine doses: if into an arm, into the ventral region of the forearm; if into a leg, into the anterior region just above the knee. A single dose of cyclophosphamide (300 mg/m$^2$) is given as a rapid (5-10 min) intravenous infusion on Day 7. Beginning on Day 10, subsequent vaccine doses 2-8 are administered weekly, followed by one booster at month 6. The vaccine is equally distributed into three intradermal sites, 1-2 cm apart. All vaccine injections will be given into the same region, separated from previous injections by 1-2 cm. Ordinarily, the injection site will be the upper dorsal arm, but not on the side of a lymph node dissection. Patients who have undergone bilateral axillary node dissection will be injected in the upper lateral thigh. Routine laboratory assays (e.g, hematology (CBC with differential platelet count), chemistry (BUN or creatinine, LDH, SGOT, alkaline phosphatase, electrolytes), and hepatitis), physical examinations, and clinical evaluations (e.g., CT/MRI of head-chest-abdomen-pelvis) are conducted regularly over a period of 5 years. The vaccine study is shown in FIG. 1.

Evaluation. An analysis evaluating relapse-free survival will be the primary efficacy endpoint. In addition, overall survival and tolerance will be evaluated. The incidence of relapse is calculated with the Kaplan-Meier's product-limit method.

Example 2

Pretreatment with BCG-free Haptenized Tumor Cells Improves Therapeutic Outcome

Anti-metastatic effects are induced by DNP-modified, irradiated, autologous tumor cell vaccine (preceded by low-dose cyclophosphamide) in a newly developed animal model, (described in co-pending application Ser. No. 60/180,257, attorney docket No. 1225/0G680, filed on Feb. 4, 2000). This animal model, particularly useful for providing information on the effectiveness of postsurgical immunotherapies for recurrence of metastatic disease, was used to evaluate whether a modified protocol could offer even greater therapeutic benefits. Specifically, treatment regimen (A), consisting of low-dose cyclophosphamide followed by unmodified or DNP-modified autologous (syngeneic) tumor cell vaccine, was compared to a new pretreatment regimen (B), in which a single dose of autologous DNP-modified tumor cells (free of BCG) was administered prior to initiation of the low-dose cyclophosphamide treatment, followed by unmodified or DNP-modified autologous tumor cell vaccine.

Materials and Methods

Tumor cells. The highly metastatic 410.4 tumor (See, e.g., Miller et al., Invasion Metastasis 1981;1:220, Pulaski et al., Cancer Res 1998;58:1486, and Miller, Cancer Res 1978;38: 3758), originating from a spontaneously arising murine mammary carcinoma (See, e.g., Heppner et al., Cancer Res 1978;38:3758, and Miller et al., Cancer Res 1981;41:3863), was used. Tumor cells were maintained in vitro at 37° C. in 5% $CO_2$ in Falcon 75 cm$^2$ polystyrene tissue culture flasks (Becton Dickinson Labware, Franklin lakes, N.J.) in Dulbecco's modified Eagle medium (DMEM) supplemented with 10% fetal bovine serum and 100 units/ml penicillin and 100 μg/ml streptomycin. Every 2-3 days the tumor cells were detached with trypsin-EDTA solution (Life Technologies Inc., Grand Island, N.Y.) and $2.0\times10^6$ cells in 20 ml of medium were seeded per new flask.

In vivo tumor model. In vitro cultured 410.4 tumor cells were detached with trypsin-EDTA, and $3\times10^5$ 410.4 tumor cells in 0.2 ml RPMI-1640 medium (Life Technologies Inc.) were injected into the mammary fatpads of female BALB/cAnNCrlBR mice, 7-10 weeks old (Charles Rivers Breeding Laboratories, Wilmington, Mass.). When tumors reached 6-8 mm in diameter, the tumors were surgically excised. Unless otherwise stated, 5-8 days after tumor excision, the mice were divided into groups and subjected to our experimental design.

Vaccine preparation. On the day of vaccination, in vitro cultured 410.4 tumor cells were detached with 0.02% EDTA solution (without trypsin) (Sigma Chemical Co., St Louis, Mo.) followed by forceful pipetting, and the tumor cells were then subjected to γ-irradiation (2500 cGY from a Cesium-137 source (J. L. Sepherd and Associates, Model 143-68 irradiator). Subsequently, an aliquot of the γ-irradiated 410.4 cells was DNP modified by exposure to dinitrofluorobenzene (DNFB, Sigma Chemicals Co., St. Louis, Mo.), according to the protocol of Berd et al. (J Clin Oncol 1997;15:2359). Each vaccine was administered in a total volume of 0.2 ml and consisted of 3-5×10$^6$ unmodified or DNP-modified, γ-irradiated, tumor cells admixed with 0.5 to 4×10$^6$ colony-forming units (CFU) of BCG, Tice strain.

Treatment protocols. (A) Non-pretreatment protocol. Unless otherwise stated, on day five to eight after tumor excision mice received an intraperitoneal (i.p.) injection of 15 mg/kg cyclophosphamide. Three days after the low-dose cyclophosphamide treatment, the mice received a subcutaneous (s.c.) injection of unmodified, or DNP-modified, irradiated, autologous tumor cell vaccine close to the site of tumor excision. This protocol was repeated every 10 days for the duration of the experiment. The mice were monitored twice a week for the appearance of visible metastases and the results are presented as percentage of relapse-free survival among all mice subjected to the same treatment protocol.

(B) Pretreatment protocol. The pretreatment protocol consisted of a single s.c. injection of 1×10$^6$ DNP-modified, irradiated, autologous tumor cell (free of BCG) administered on the back of the mice on day 3-7 after the excision of the primary tumor. Three to seven days later, the mice received an i.p. injection of 15 mg/kg cyclophosphamide (Mead Johnson—A Bristol-Myers Squibb Co., Princeton, N.J.). Three days after the low-dose cyclophosphamide treatment, the mice received a s.c. injection of unmodified, or DNP-modified, irradiated, autologous tumor cell vaccine close to the site of tumor excision. This protocol was repeated every 10 days for the duration of the experiment. The mice were monitored twice a week for the appearance of visible metastases and the results are presented as percentage of relapse-free survival among all mice subjected to the same treatment protocol.

Statistical analysis. The percentages of relapse-free survival of mice subjected to different treatment protocols were compared at various time points after tumor excision by the use of a paired Student's T-test. A p value of 0.05 or lower was considered significant.

Results

Protocol A only. Treatment of mice (from which the primary tumor was surgically excised) with low-dose cyclophosphamide followed by DNP-modified, irradiated, autologous tumor cell vaccine led to a significantly better relapse-free survival than treatment of such mice with low-dose cyclophosphamide followed by unmodified, irradiated, autologous tumor cell vaccine (p=0.005).

Protocol A vs Protocol B. Pretreatment of mice with DNP-modified, irradiated, autologous tumor cells (without BCG) 3-7 days prior to the initiation of the low-dose cyclophosphamide treatment followed by DNP-modified, -irradiated, autologous tumor cell vaccine resulted in a significant improvement in the relapse-free survival relative to that observed in mice that received low-dose cyclophosphamide followed by DNP-modified, irradiated, autologous tumor cell vaccine without the pretreatment regimen (p=0.002).

Conclusion. The results illustrated that Protocol B offered additional therapeutic benefits in the described tumor model of metastatic disease as compared to Protocol A, suggesting that a pretreatment protocol, where haptenized tumor cells are administered prior to cyclophosphamide and additional vaccine doses, may offer further therapeutic benefits also in patients with metastatic melanoma.

Example 3

The Timing of an Haptenized or Non-Haptenized, Irradiated, Autologous, Melanoma, Tumor Cell Treatment Prior to Administration of an Immunomodulator and an Haptenized Vaccine Improves Therapeutic Outcome The anti-metastatic effects of hapten-modified vaccines are increased by the administration of a "priming" induction dose administered several days before administration of a low dose of the immunomodulator cyclophosphamide (CY) and DNP vaccine mixed with BCG. The induction (or "priming") dose comprised of one of the three following compositions: (1) 10$^6$ irradiated, autologous, tumor cells (AU TC); (2) a mixture of irradiated, autologous, tumor cells and irradiated, autologous, DNP-modified tumor cells 10$^6$ of each; or (3) 10$^6$ irradiated, autologous, DNP-modified tumor cells.

Material and Methods

Patient group. The treatment efficacy of administering a "priming" induction dose of haptenized or non-haptenized or a mixture of haptenized and non-haptenized, irradiated, autologous, tumor-cells before administration of a haptenized vaccine was studied in 214 post-surgical melanoma patients having bulky, regional, lymph-node metastases. Prior to the initiation of the vaccine treatment, preferably within two months from the starting point, one or more of the tumor masses was surgically resected from each patient. An adequate tumor sample, approximately 2 cm or 5 g, yielding at least about 50×10$^6$ cells, was kept under sterile conditions to be used for vaccine preparation. Vaccines were prepared according to methods outlined in Example 1. Patients were preferably confirmed melanoma-free by computed tomography (CT) or magnetic resonance imaging (MRI).

Treatment protocols. Three protocols were used to evaluate whether a pre-treatment induction dose administered several days before the administration of low-dose cyclophosphamide and DNP-vaccine mixed with BCG offers greater therapeutic effects than protocols without a pre-treatment induction dose. The induction (or "priming") dose comprised one of the three following compositions: (1) 10$^6$ irradiated, autologous, tumor cells (AU TC); (2) a mixture of irradiated, autologous, tumor cells and irradiated, autologous, DNP-modified tumor cells (10$^6$ of each); or (3) 10$^6$ irradiated, autologous, DNP-modified tumor cells;

Protocol A (124 patients): All patients were administered a low-dose of cyclophosphamide (300 mg/m$^2$) intravenously, followed by multiple, intradermal injections of DNP-vaccine (dose range: 2.5-25.0×10$^6$ irradiated AUTC) mixed with BCG three days after the low-dose of cyclophosphamide. The "priming" dose was administered as an intradermal injection into the ventral forearm of the patient days prior to CY. Protocol B (27 patients): The primary dose was administered on the same day as CY. Protocol C (43 patients): The primary dose was administered at the time points (A+B).

Results

Protocol A, which included administration of a "priming" induction dose comprising one of the three following compositions: (1) $10^6$ irradiated, autologous, tumor cells (AU TC); (2) a mixture of $10^6$ each of irradiated autologous, tumor cells and irradiated, autologous, DNP-modified tumor cells; or (3) $10^6$ irradiated, autologous, DNP-modified tumor cells (the preferred reduction composition) several days before administration of a low dose of cyclophosphamide (CY) and DNP-modified, irradiated, autologous tumor cells mixed with BCG led to a significantly better relapse-free survival rate than with protocols in which a primary composition was administered on the same day as cyclophosphamide (or omitted altogether). For Protocol A, the 5 year relapse-free survival rate was 41% versus 18% in Groups B and C, which received a primary dose on the same day as CY (p=0.1, log rank test). Multi-variate analysis (Cox regression) showed that the difference in relapse-free survival was not attributable an imbalance of known prognostic variables (number of (+) nodes) between the patient groups treated under each protocol.

Furthermore, the proportion of patients who developed (+) delayed-type sensitivity ($\geq 5$ mm diameter induration) was 81/115=70.4% (p<0.001, Fisher's exact test), which is significantly higher than the (+) DTH response rates of protocols with the "priming" dose the same day as CY. The proportion of patients who developed (+) delayed-type sensitivity ($\geq 5$ mm diameter induration) under Protocol C was 10/51=19.6% (p<0.001, Fisher's exact test). Since it has been shown that development of (+) DTH response to DNP modified or unmodified AU TC following vaccine treatment was significantly associated with longer survival, the "priming" induction dose comprising one of the three following compositions: (1) irradiated, autologous, tumor cells (AUTC); (2) a mixture of irradiated, autologous, tumor cells and irradiated, autologous, DNP-modified tumor cells; and (3) DNP-modified tumor cells irradiated, autologous, tumor cells as in Protocol A, increases the chances of patient survival by increasing (+) DTH response rates.

The timing of the "priming" induction dose several days prior to administration of a low-dose of cyclophosphamide and not near or on the same day as CY apparently determines whether the subsequent course of DNP-vaccine results in tumor immunity or unresponsiveness.

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims.

It is further to be understood that all numerical values are approximate and are provided for description only.

Patents, patent applications, and publications cited throughout this application are incorporated herein by reference in their entireties.

What is claimed is:

1. A method for inducing an anti-tumor response in a human patient suffering from a tumor, which method comprises administering to the patient in the following order:
   (a) on the first day of treatment, a first composition comprising from about $2 \times 10^5$ to $2.5 \times 10^6$ of at least one of autologous tumor cells or autologous tumor cell equivalents free from any adjuvant;
   (b) four to seven days after initiation of the treatment, cyclophosphamide; and
   (c) at least one week after initiation of the treatment, a second composition comprising an adjuvant and from about $2 \times 10^5$ to about $1 \times 10^7$ of at least one of autologous tumor cells or tumor cell equivalents, wherein said tumor cells or tumor cell equivalents are conjugated to hapten, wherein the hapten is selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, sulfanilic acid, arsanilic acid, dinitrobenzene-S-mustard and combinations thereof, wherein said method results in at least one of an anti-tumor response, therapeutic regression of a tumor or prevention of tumor progression.

2. The method in claim 1, in which the adjuvant in said step (c) is *Bacille Calmette-Guerin*.

3. The method of claim 1, wherein the tumor cells or tumor cell equivalents in said step (a) are haptenized with a hapten selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, sulfanilic acid, arsanilic acid, dinitrobenzene-S-mustard and combinations thereof.

4. The method of claim 1, wherein the tumor cells or tumor cell equivalents in said step (a) are a mixture of haptenized and non-haptenized tumor cells or tumor cell equivalents.

5. The method of claim 1, wherein the hapten is dinitrophenyl.

6. The method of claim 1, wherein the adjuvant in said step (c) is selected from the group consisting of *Bacille Calmette-Guerin*, Q-21, and detoxified endotoxin.

7. The method of claim 1, wherein the cyclophosphamide is administered 5 to 7 days after administration of the first composition.

8. The method of claim 1, wherein the tumor cells or tumor cell equivalents originate from a tumor selected from the group consisting of melanoma, ovarian cancer, colon cancer, breast cancer, rectal cancer, lung cancer, kidney cancer, prostate cancer, and leukemia.

9. The method of clam 8, wherein the tumor is melanoma.

10. The method of claim 8, wherein the tumor is ovarian cancer.

11. The method of claim 1, wherein the tumor cell or tumor cell equivalents are rendered incapable of growth or multiplication in vivo.

12. The method of claim 11, wherein the tumor cell or tumor cell equivalents are rendered incapable of growth or multiplication in vivo by irradiation.

13. The method of claim 11, wherein the tumor cells or tumor cell equivalents are rendered incapable of growth or multiplication in vivo by haptenization.

14. A method for inducing an anti-tumor response in a human patient suffering from a tumor, which method comprises administering to the patient in the following order:
   (a) a composition comprising from about $2 \times 10^5$ to about $2.5 \times 10^6$ of at least one of tumor cells or tumor cell equivalents per dose, without any adjuvant, wherein the tumor cells or tumor cell equivalents are conjugated to a hapten, and rendered incapable of growth or multiplication in vivo;
   (b) cyclophosphamide; and
   (c) a second composition comprising an adjuvant and from about $2 \times 10^5$ to about $1 \times 10^7$ of at least one of tumor cells or tumor cell equivalents, wherein the tumor cell or tumor cell equivalents are conjugated to a hapten, wherein the hapten in steps (a) and (c) is the same or different, and is selected from the group consisting of dinitrophenyl, trinitrophenyl, N-iodoacetyl-N'-(5-sulfonic 1-naphthyl) ethylene diamine, trinitrobenzenesulfonic acid, fluorescein isothiocyanate, arsenic acid benzene isothiocyanate, sulfanilic acid, arsanilic acid, dinitrobenzene-S-mustard and combinations thereof, and wherein said method results in at least one of an anti-tumor response, therapeutic regression of a tumor or prevention of tumor progression.

15. The method of claim 14, wherein the hapten in said steps (a) and (c) is dinitrophenyl.

16. The method of claim 14, wherein the tumor is melanoma.

17. The method of claim 14, wherein the tumor is ovarian cancer.

18. The method of claim 14, wherein the adjuvant is selected from the group consisting of *Bacille-Calmette-Guerin*, Q-21, and detoxified endotoxin.

19. A method for inducing an anti-tumor response in a mammalian patient suffering from a tumor, which, method comprises administering to the patient:

(a) on the first day of treatment, a composition comprising $2 \times 10^5$ to $2.5 \times 10^6$ haptenized autologous tumor cells free from any adjuvant;

(b) four to seven days after initiation of the treatment, cyclophosphamide; and (c) at least one week after initiation of the treatment, a second composition comprising an adjuvant and $2 \times 10^5$ to $1 \times 10^7$ haptenized autologous tumor cells wherein the cells in said steps (a) and (c) are haptenized with dinitrophenyl, and wherein said method results in at least one of an anti-tumor response, therapeutic regression of a tumor or prevention of tumor progression.

20. The method of claim 19, in which the adjuvant in said step (c) is Bacille Calmette-*Guerin*.

* * * * *